US008147427B2

(12) United States Patent
Nanto et al.

(10) Patent No.: US 8,147,427 B2
(45) Date of Patent: Apr. 3, 2012

(54) GUIDEWIRES TWIST RELEASING DEVICE

(75) Inventors: Shinsuke Nanto, Nishinomiya (JP); Satoru Mori, Osaka (JP)

(73) Assignee: Nipro Corporation, Osaka (JP)

(*) Notice: Subject to any disclaimer, the term of this patent is extended or adjusted under 35 U.S.C. 154(b) by 123 days.

(21) Appl. No.: 12/661,665

(22) Filed: Mar. 22, 2010

(65) Prior Publication Data
US 2010/0286565 A1 Nov. 11, 2010

(30) Foreign Application Priority Data

Mar. 27, 2009 (JP) .................................. 2009-080656

(51) Int. Cl.
*A61M 25/00* (2006.01)

(52) U.S. Cl. ............................. 600/585; 705/16; 705/24

(58) Field of Classification Search .................. 600/433, 600/434, 585; 604/164.13
See application file for complete search history.

(56) References Cited

U.S. PATENT DOCUMENTS

| 7,744,588 B2 * | 6/2010 | Nash et al. ..................... 604/533 |
| 2005/0197663 A1 * | 9/2005 | Soma et al. ..................... 606/108 |
| 2006/0270977 A1 * | 11/2006 | Fisher et al. .............. 604/103.04 |
| 2007/0250001 A1 | 10/2007 | Hilaire et al. |

FOREIGN PATENT DOCUMENTS

JP 2006-326226 12/2006

* cited by examiner

*Primary Examiner* — Max Hindenburg
*Assistant Examiner* — Jonathan M. Foreman
(74) *Attorney, Agent, or Firm* — Jordan and Hamburg LLP

(57) ABSTRACT

To provide a means capable easily releasing twist of two or more guidewires passed through a guiding catheter without pulling out the guidewires. A twist releasing apparatus has a shaft, a first tube formed at the tip of the shaft and has a first lumen through which two or more guidewires can be passed, a second tube disposed through a gap at the tip side in the axis direction relative to the first tube and has a second lumen through the two or more guidewires can be passed, and a connection portion for connecting the first tube and the second tube so that the two or more guidewires can be passed through the first lumen and the second lumen. The second tube has a slit that is formed in an axis direction and can be elastically deformed. The connection portion can be elastically deformed into a curved shape in the axis direction.

14 Claims, 13 Drawing Sheets

GUIDEWIRES TWIST RELEASING DEVICE

BACKGROUND OF THE INVENTION

The present invention relates to a device for releasing twist of two or more guidewires passed through a guiding catheter.

Heretofore, medical treatment has been performed in which a catheter is inserted to blood vessels to locally give pharmaceutical drugs or expand narrowing of the blood vessels. For example, in order to expand a narrowed portion of the coronary arteries with a balloon catheter in the percutaneous transluminal coronary angioplasty (PTCA), a sheath introducer is inserted to the arterial blood vessel by a Seldinger technique or the like to secure the arterial blood vessel from the outside of the body. Then, an imaging guidewire is inserted to the vicinity of the heart. Subsequently, a guiding catheter is inserted as is guided by the imaging guidewire, so that the tip thereof is positioned at the entrance of the coronary arteries. Then, the imaging guidewire is pulled out, and a guidewire for PTCA (hereinafter sometimes simply referred to as a "guidewire".) is inserted to the guiding catheter, so that the tip thereof is positioned at the vicinity of the narrowed portion. A balloon catheter is inserted to the guiding catheter as is guided by the guidewire, so that balloon portion is positioned at the narrowed portion of the coronary arteries. Thereafter, the balloon portion is inflated to expand the narrowed portion of the coronary arteries (Patent Document 1).

Moreover, the following technique is mentioned as a technique for expanding two or more narrowed portions in the coronary arteries. According to the technique, two or more guidewires are inserted to the guiding catheter inserted to the arterial blood vessel as described above, so that the tip of each guidewire is positioned at each of two or more narrowed portions in the coronary arteries. Then, two or more balloon catheters are guided by the respective guidewires to be disposed at each of the two or more narrowed portions.

Patent Document 1 Japanese Unexamined Patent Application Publication No. 2006-326226

SUMMARY OF THE INVENTION

When the guidewire is inserted to the guiding catheter to be positioned at the vicinity of a target narrowed portion of the coronary arteries as described above, the guidewire is pushed or pulled or rotated according to the branch or shape of the coronary arteries at the base end portion (hand side) of the guidewire. However, for example, two guidewires are passed through the guiding catheter, and then each guidewire is operated as described above, which may result in the fact that the two guidewires are twisted in the guiding catheter.

When the two guidewires are twisted in the guiding catheter, the balloon catheter cannot be inserted, as guided by the guidewire, to the top end from the twisted portion. Therefore, it is necessary to release the twist of the guidewires. Heretofore, the operation for releasing the twist of the guidewires has depended on the intuition of the operator. However, even in the case of a skilled operator, the twist of the guidewires cannot be released in some cases. In such a case, an operation of pulling out one of the guidewires once, and then inserting the guidewire again has been required.

The present invention has been made in view of the above-described circumstances. It is an object of the present invention to provide a member capable of easily releasing the twist of two or more guidewires passed through a guiding catheter without pulling out the guidewires.

(1) A guidewires twist releasing device according to the invention releases twist of two or more guidewires passed through a guiding catheter. The device has: a long member that can be inserted to/pulled out from the guiding catheter; a first tubular body that is provided at the tip of the long member in such a manner as to be inserted to/pulled out from the guiding catheter and has a first lumen through which the two or more guidewires can be passed; a second tubular body that is disposed through a gap at the tip side, relative to the first tubular body in the axis direction of the first tubular body in such a manner as to be inserted to/pulled out from the guiding catheter and has a second lumen through which the two or more guidewires can be passed; and a connection member for connecting the first tubular body and the second tubular body so that the two or more guidewires can be continuously passed through the first lumen and the second lumen. The second tubular body has a slit formed in the axis direction and can be elastically deformed so that the slit opens. The connection member can be elastically deformed into a curved shape in the axis direction of the first tubular body.

When two or more guidewires are passed through the guiding catheter and then are twisted, the guidewires twist releasing device releases the twist of the two or more guidewires when inserted to/pulled out from the guiding catheter. Therefore, when the device is used, the guiding catheter is inserted to the arterial blood vessel or the like, the two or more guidewires are passed through the guiding catheter, and the tip of each guidewire reaches a target treatment area of the coronary arteries or the like.

In the device, the first tubular body, the connection member, and the second tubular body are disposed at the tip of the long member that can be inserted to/pulled out from the guiding catheter. As the long member, stainless steel bar-shaped materials, synthetic resin tube materials, etc., can be employed as appropriate insofar as the first tubular body, the connection member, and the second tubular body can be inserted to/pulled out from the guiding catheter. The long member may be constituted as a tube integrated with the first tubular body. Furthermore, for ease of operation, a publicly handle or the like may be provided at a handling side of the long member.

The first tubular body has the first lumen through which the two or more guidewires passed through the guiding catheter can be passed. Similarly, the second tubular body has the second lumen through which the two or more guidewires passed through the guiding catheter can be passed. The connection member connects the first tubular body and the second tubular body in the axis direction through a gap in an arrangement where the two or more guidewires can be continuously passed through the first lumen and the second lumen. Therefore, the guidewires passed through the first lumen and the second lumen are exposed to the outside in the gap between the first tubular body and the second tubular body.

The second tubular body is provided with a slit formed along the axis direction. The slit is closed in a usual state where external force is not applied, and thus second lumen of the second tubular body becomes a substantially closed space. In contrast, when external force is applied in the direction of opening the slit, the second tubular body is elastically deformed to open the slit. Thus, the second lumen of the second tubular body becomes a space opened in the axis direction by the slit. As described above, in a state where the two or more guidewires are passed through the first lumen and the second lumen, the slit is closed.

At the hand side of the guiding catheter, the two or more guidewires are passed through the first lumen and the second lumen of the device. Then, the hand side of the long member is operated, so that the first tubular body, the connection member, and the second tubular body are inserted to the guiding catheter with the second tubular body positioned at the head. The first tubular body, the connection member, and the second tubular body are projected from the tip of the guiding catheter to be inserted to the coronary arteries or the like while being guided by the two or more guidewires. In this case, although the two or more guidewires are twisted in the guiding catheter, the two or more guidewires pass through the first lumen and the second lumen while being twisted.

As described above, each guidewire projected from the tip of the guiding catheter is inserted to a target treatment site of each guidewire at the branch portion or the like of blood vessels. When the first tubular body, the connection member, and the second tubular body in which the respective guidewires are integrally passed through the first lumen and the second lumen reach the branch portion of the respective blood vessels where the two or more guidewires are separately inserted, the second tubular body positioned at the head in the insertion direction is guided by one of the two or more guidewires to move to the blood vessel to which the one guidewire is inserted. In this case, the force of enlarging the diameter of the second lumen acts on the second tubular body by the other guidewires inserted to other blood vessels, and the second tubular body is elastically deformed by the force to open the slit. Therefore, the second tubular body moves to the blood vessel through which one guidewire is inserted and simultaneously the other guidewires move in the axis direction of the second tubular body while passing through the opened slit to come out from the second lumen. Thus, only one guidewire is passed through the first lumen and the second lumen, and the other guidewires are passed through only the first lumen and are projected from the gap between the first tubular body and the second tubular body. Only the second tubular body moves to the blood vessel to which one guidewire is inserted and the first tubular body remains at the branch portion of the blood vessels where one guidewire and the other guidewires are divided. In this case, the connection member is in a shape of curving the second tubular body in the axis direction relative to the first tubular body, which allows only the second tubular body to move to the blood vessel through which one guidewire is inserted.

As described above, after only one guidewire is passed through the first lumen and the second lumen and the other guidewires are passed through only the first lumen and are projected from the gap between the first tubular body and the second tubular body, the hand side of the long member is operated to pull out the first tubular body, the connection member, and the second tubular body from the guiding catheter. Thus, in a state where only one guidewire is passed through the first lumen and the second lumen and the other guidewires are passed through only the first lumen and are projected from the gap between the first tubular body and the second tubular body, the first tubular body, the connection member, and the second tubular body are first settled in the guiding catheter, move toward the hand side in the guiding catheter, and are disconnected from the hand side of the guiding catheter. When pulled out as described above, only one guidewire among the two or more guidewires in the guiding catheter passes through the second lumen, and the other guidewires pass through the gap between the first tubular body and the second tubular body without passing through the second lumen. More specifically, one guidewire and the other guidewires pass though different paths in the first lumen and the second lumen. Thus, the twist of one guidewire and the other guidewires is released.

When two guidewires are passed through the guiding catheter and are twisted, the twist of the two guidewires is released by the above-described operation. However, for example, when three guidewires are passed and are twisted, in order to release the twist of the remaining two guidewires equivalent to the above-described other guidewires, the twist of the other two guidewires is released by passing only one guidewire of the other two guidewires through the second lumen in the same manner as the operation for releasing the twist of one guidewire.

(2) At a first end facing the first tubular body among both the ends in the axis direction of the second tubular body, a protrusion in which one portion where the slit is formed extends in the axis direction may be provided.

As described above, when the twist of the two or more guidewires is released, the other guidewires are passed through only the first lumen and are projected from the gap between the first tubular body and the second tubular body to the outside. When the first tubular body, the connection member, and the second tubular body are pulled out from the guiding catheter, the other guidewires can contact the first end of the second tubular body. At the first end, a portion in which one portion where the slit is formed extends along the axis direction is provided. The direction in which the protrusion extends from the first end serves as the direction in which the first tubular body, the connection member, and the second tubular body are pulled out. In order for the other guidewires to enter the slit passing over the protrusion, the other guidewires need to move in the direction in which the first tubular body, the connection member, and the second tubular body are pulled out. Therefore, when the first tubular body, the connection member, and the second tubular body are pulled out, the other guidewires accidentally enter the slit and the entry into the second lumen is suppressed.

(3) At a second end not facing the first tubular body among both the ends in the axis direction of the second tubular body, a recess in which one portion where the slit is formed is recessed in the axis direction may be provided.

As described above, when the twist of the two or more guidewires is released, the other guidewires move in the axis direction of the second tubular body while passing through the opened slit to come out from the second lumen. In this case, the other guidewires enter the slit from the second end of the second tubular body. At the second end, the recess in which one portion where the slit is formed is recessed along the axis direction is provided, and thus the recess serves as a guiding portion to facilitate the entry of the other guidewires into the slit.

(4) The first tubular body, the second tubular body, and the connection member may be formed into an integral tubular body.

For example, a part of the peripheral wall of the tubular body is notched, parts of the tubular body divided by the notch in the axis direction are formed into the first tubular body and the second tubular body, and a part of the peripheral wall left by the notch is formed into as the connection member, whereby the guidewire twist releasing device is constituted. Thus, since the first tubular body, the connection member, and the second tubular body can be produced from one tubular body, the production of the device is facilitated. Moreover, projection portions, such as projections or level differences, can be reduced as much as possible in the outer shape of the first tubular body, the connection member, and the second tubular body, the first tubular body, the connection member, and the second tubular body that hardly damage blood vessels can be achieved.

(5) The first tubular body may have a sub-lumen serving as another space different from the first lumen, and a core material may be provided in the sub-lumen.

Since the first tubular body is supported by the core material along the axis direction, the first tubular body becomes difficult to buckle during the operation. Moreover, since the core material is provided at the sub-lumen serving as another space different from the first lumen, the core material is not twisted with the two or more guidewires.

(6) A marker detectable by radiation may be provided at least either one of the first tubular body or the second tubular body.

The marker detectable by radiation is achieved by, for example, mixing particles of an X-ray imaging element with materials of the first tubular body or the second tubular body or embedding an X-ray impermeable metal member in the first tubular body or the second tubular body. Thus, an operation can be performed while confirming the position of the first tubular body or the second tubular body in blood vessels by, for example, X-ray imaging.

According to the invention of the guidewires twist releasing device, the two or more guidewires twisted in the guiding catheter are passed through the first lumen and the second lumen, the first tubular body, the connection member, and the second tubular body are inserted to the guiding catheter to be projected from the tip of the guiding catheter with the second tubular body positioned at the head, only the second tubular body is guided by any one the two or more guidewires to be directed to the blood vessel to which the one guidewire is inserted, the other guidewires are passed through the slit of the second tubular body to be pulled out from the second lumen, only the one guidewire is passed through the first lumen and the second lumen, and the other guidewires are passed through only the first lumen and projected from the gap between the first tubular body and the second tubular body. Then, in the state, when the first tubular body, the connection member, and the second tubular body are pulled out from the guiding catheter, the twist of the one guidewire and the other guidewires is released. Therefore, the twist of the two or more guidewires passed through the guiding catheter can be easily released without pulling out the guidewires.

DESCRIPTION OF THE PREFERRED EMBODIMENTS

Hereinafter, preferable embodiments of the invention will be described. This embodiment is merely one embodiment of the invention, and it is a matter of course that the embodiment can be modified insofar as the gist of the invention is not changed.

Figure 1:
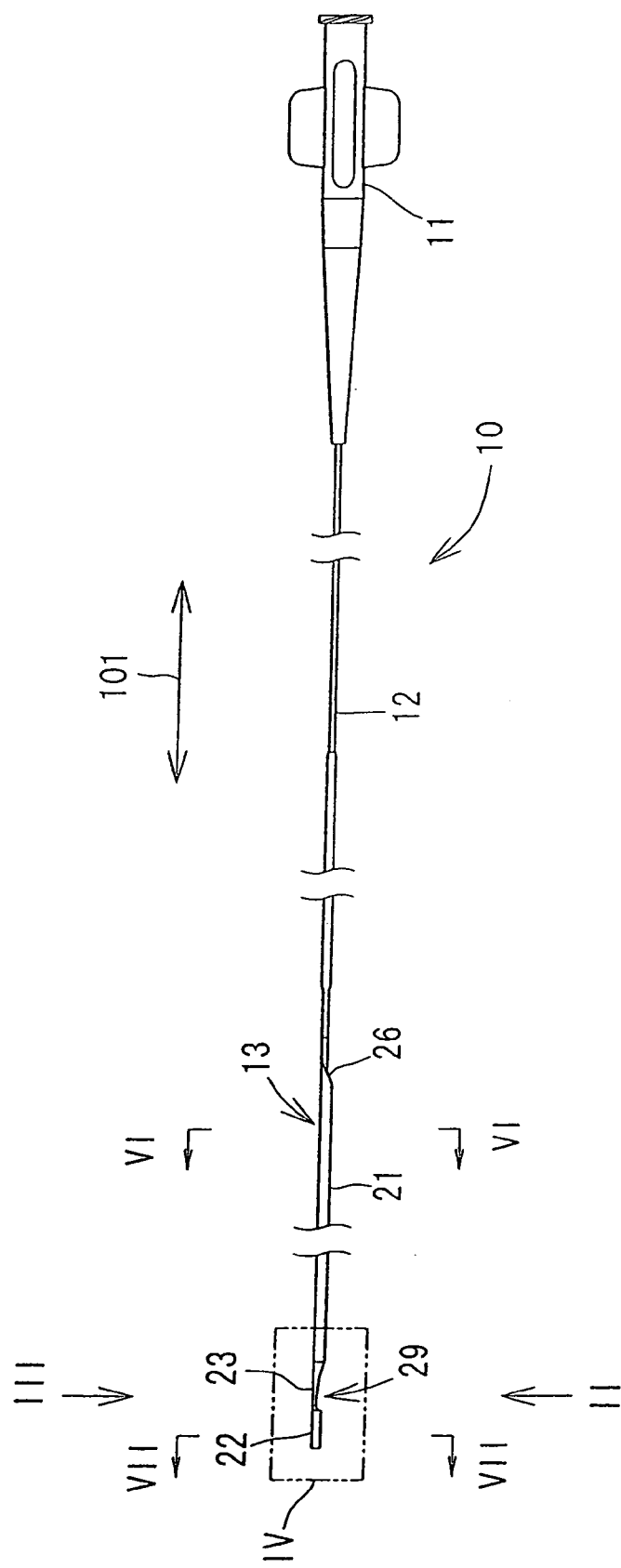
FIG. 1 is a plan view showing the external structure of a twist releasing apparatus 10 according to the embodiment of the invention.
Figure 2:
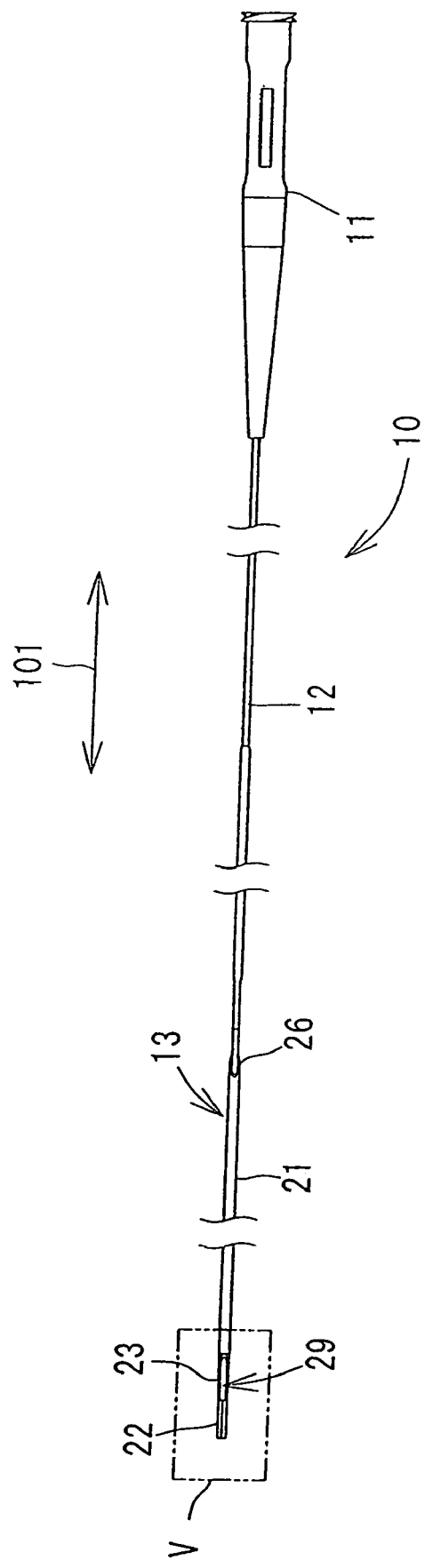
FIG. 2 is a side view of the twist releasing apparatus 10 as viewed along arrow II in FIG. 1.
Figure 3:
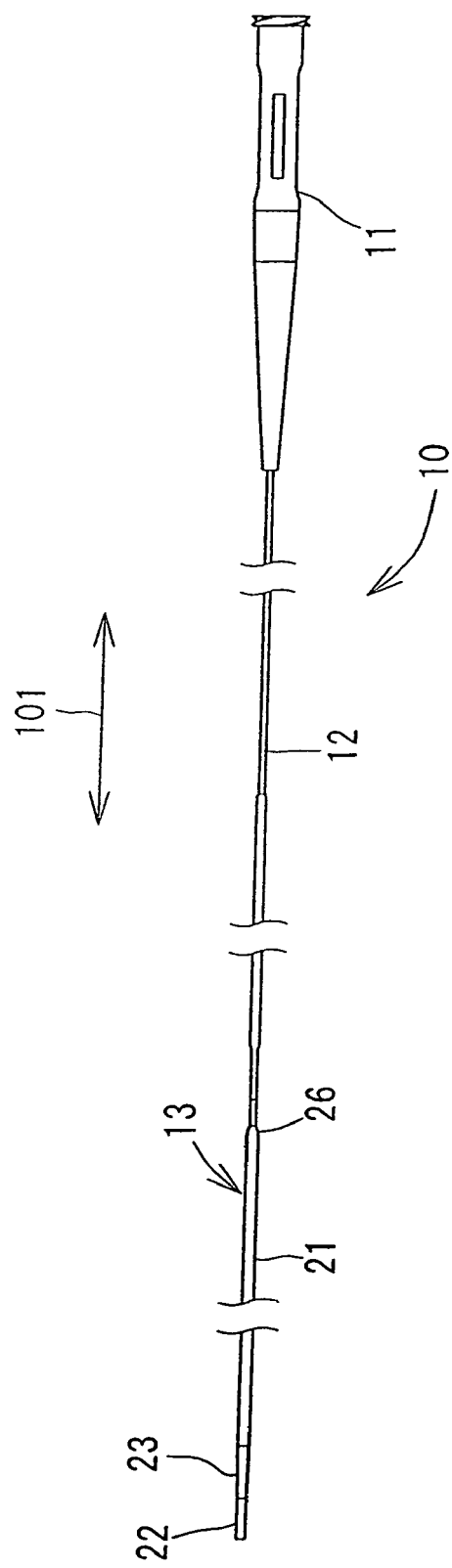
FIG. 3 is a side view of the twist releasing apparatus 10 as viewed along arrow III in FIG. 1.

FIGS. 1 to 3 show a twist releasing apparatus 10 according to this embodiment. The twist releasing apparatus 10 releases twist of two or more guidewires passed through a guiding catheter (not shown). The twist releasing apparatus 10 is equivalent to the guidewire twist releasing device according to the invention. The twist releasing apparatus 10 mainly contains a handle portion 11, a shaft 12, and a tube 13.

The shaft 12 is a bar-shaped medical treatment stainless steel material. The shaft 12 may be coated with a fluoro resin or the like. The shaft 12 can be inserted to a guiding catheter (not shown) and has a sufficiently small outer diameter relative to the inner diameter of the guiding catheter. The shaft 12 has rigidity that allows elastic deformation in accordance with the curved shape of the arterial blood vessel or the like and that prevents buckling in the axis direction 101. The shaft 12 is equivalent to the long member of the invention.

The handle portion 11 is connected to the base end (right end of FIGS. 1 to 3) of the shaft 12. The handle portion 11 can serve as a handle when the shaft 12 is inserted to/pulled out from the guiding catheter or rotated. The handle portion 11 has a cylinder shape having an outer diameter suitable for an operating person to hold. Moreover, the handle portion 11 is provided with a blade for facilitating the rotation operation around the axis direction 101. The twist releasing apparatus 10 is not operated only by the handle portion 11 and may be operated by an operating person by, for example, handling the shaft 12.

The tube 13 is connected to the tip (left end in FIGS. 1 to 3) of the shaft 12 to extend along the axis direction 101 of the shaft 12. The tube 13 is a single tube having a so-called double-lumen structure and is a molded article of soft plastics, such as polyamide or polyether amide, that can be elastically deformed. The tube 13 has almost uniform outer diameter in the axis direction. The outer diameter is determined in a range such that the tube 13 can be passed through the guiding catheter (not shown).

The tube 13 is roughly divided to a first tube 21, a second tube 22, and a connection portion 23. The first tube 21 is equivalent to the first tubular body in the invention. The second tube 22 is equivalent to the second tubular body in the invention. The connection portion 23 is equivalent to the connection member in the invention. More specifically, in this embodiment, the first tubular body, the second tubular body, and the connection member are formed as an integral tubular body (tube 13).

Figure 6:
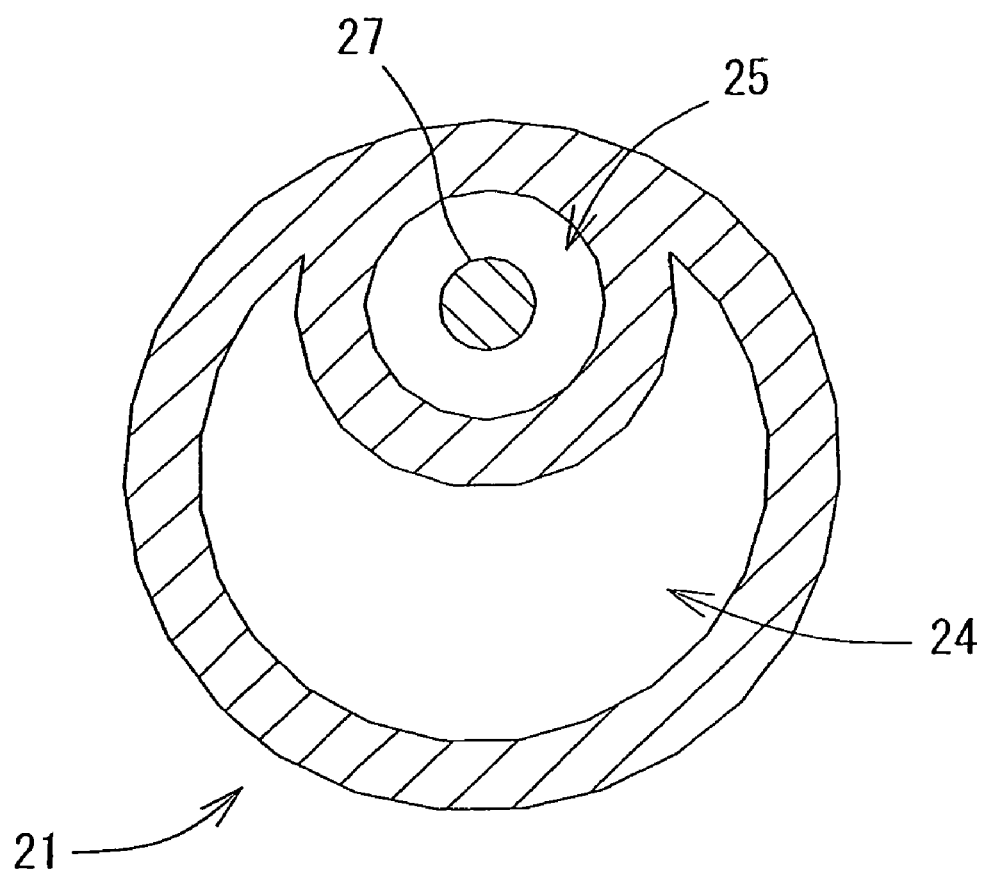
FIG. 6 is a cross sectional view showing the cross-sectional structure of a first tube 21 along the cut line VI-VI of FIG. 1.

The first tube 21 is connected to the tip of the shaft 12 to extend in the axis direction 101. The first tube 21 forms a part of the base end side in the tube 13 (right side in FIGS. 1 to 3). As shown in FIG. 6, the first tube 21 has a double lumen structure having a first lumen of 24 and a sub-lumen 25 through which the guidewire is passed. The base end 26 of the first tube 21 opens toward the base end side of the shaft 12. The first lumen 24 is opened at the base end 26. Thus, the guidewire can be passed to the first lumen 24 from the base end 26.

The sub-lumen 25 extends in the axis direction 101 as another space in the first lumen 24. The sub-lumen 25 is provided with a core material 27 in the axis direction 101. The core material 27 is a bar-shaped medical treatment stainless steel material, for example. The core material 27 has rigidity that allows elastic deformation in accordance with the curved shape of the arterial blood vessel or the like and that prevents buckling in the axis direction 101. The core material 27 may be integrally constituted with the shaft 12. The core material 27 extends in the axis direction 101 from the base end 26 of the first tube 21 to reach the vicinity of the second tube 22.

Figure 4:
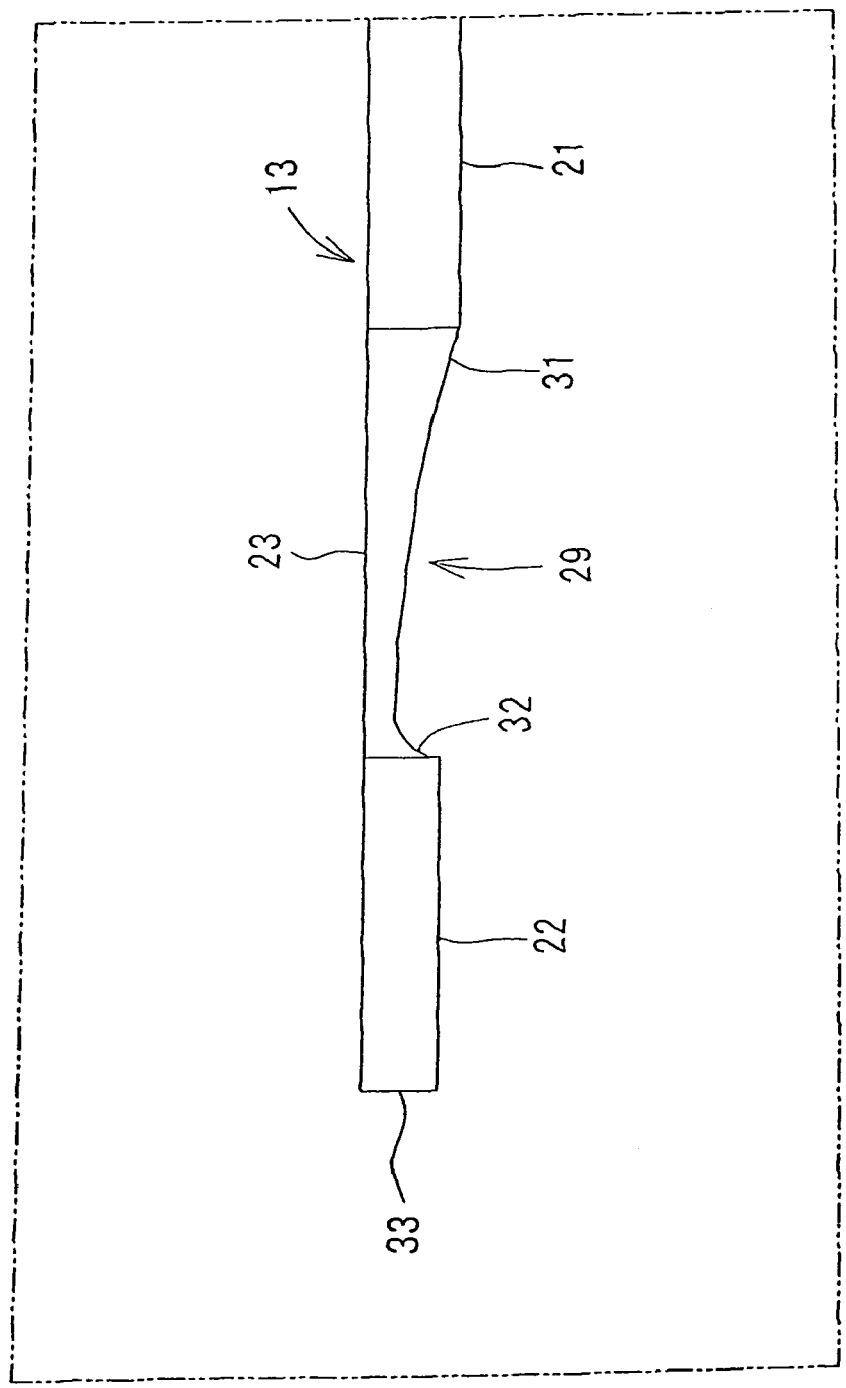
FIG. 4 is an enlarged view of a region IV in FIG. 1.
Figure 5:
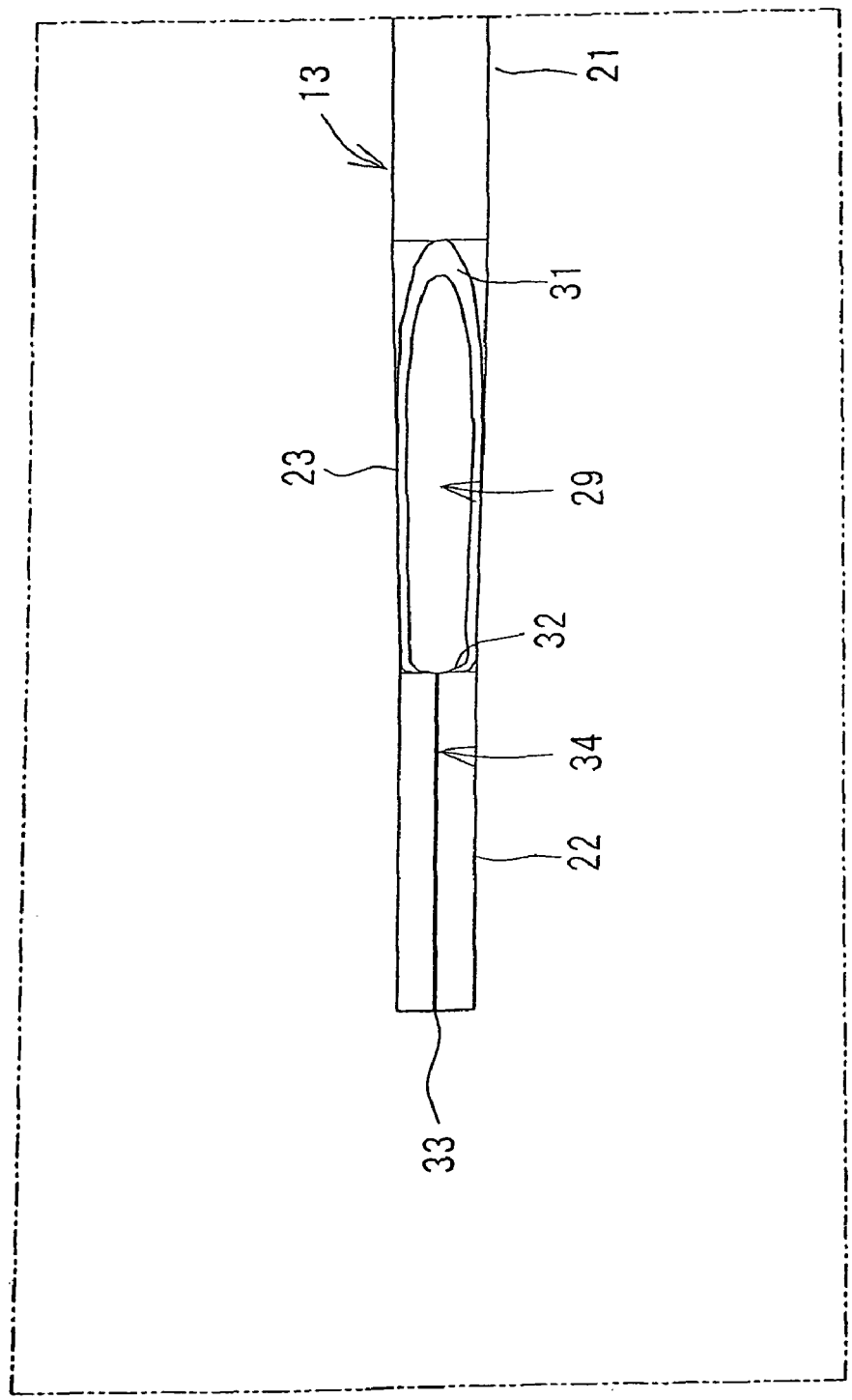
FIG. 5 is an enlarged view of a region V in FIG. 2.
Figure 7:
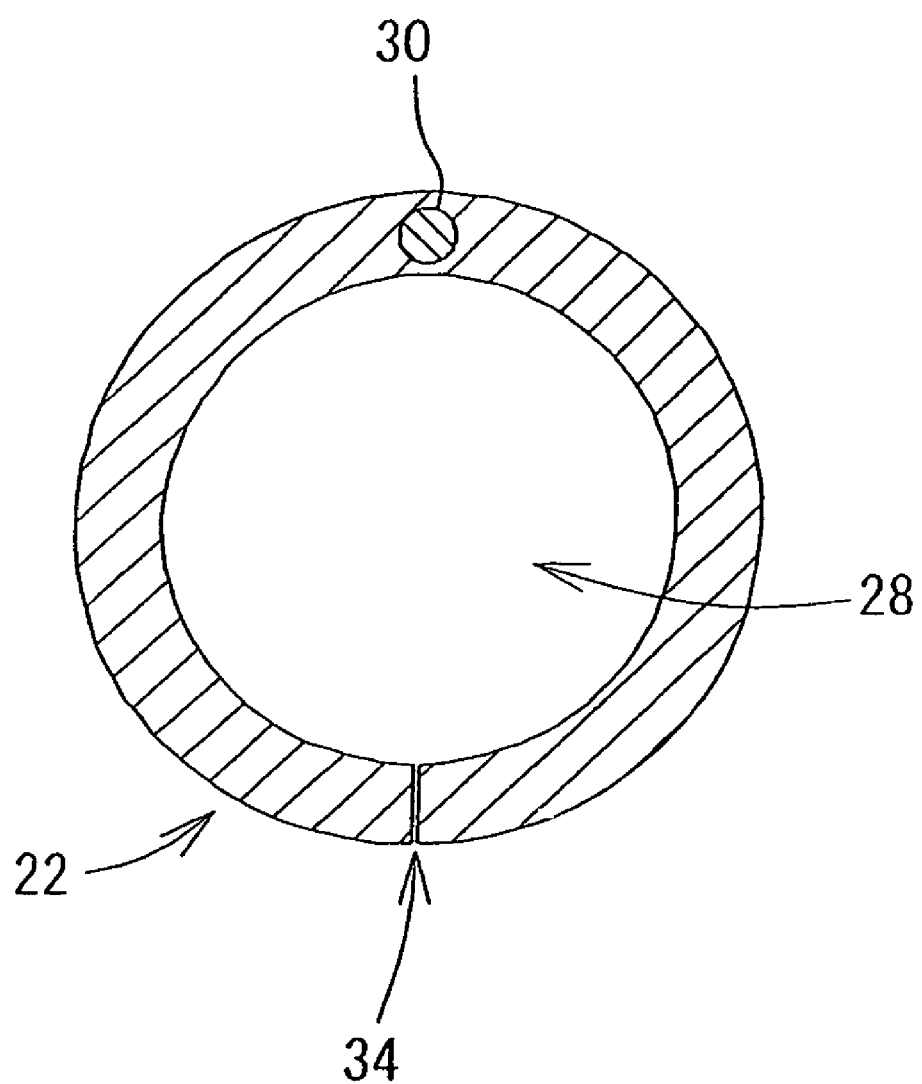
FIG. 7 is a cross sectional view showing the cross-sectional structure of a second tube 22 along the cut line VII-VII of FIG. 1.

The second tube 22 forms a part of the tip side of the tube 13 (left end side in FIGS. 1 to 3). As shown in FIG. 7, the second tube 22 has a second lumen 28 through which the guidewire is passed. The second tube 22 forms the second lumen 28 that does not form an integral lumen relative to the first lumen 24 of the first tube 22 by a notch 29 (FIGS. 4 and 5). The integral lumen refers to a space not having an opening other than both the ends of a tube. More specifically, the first lumen 24 is formed as an integral lumen by the first tube 22 and the second lumen 28 is formed, by the second tube 22, as an integral lumen that is different from the first lumen. The gap between the first tube 21 and the second tube 22 is opened by the notch 29 to the exterior space of the tube 13.

As shown in FIG. 7, an X-ray marker 30 is embedded in the peripheral wall of the second tube. The X-ray marker 30 is a bar-shaped metal material having a short length which does not allow penetration of X-rays. As a metal that does not allow penetration of X-rays, platinum, gold, tungsten, etc., and alloys thereof are mentioned, for example.

As shown in FIGS. 4 and 5, the first tube 21 and the second tube 22 are separated in the axis direction 101 by the notch 29 that opens a part of the peripheral wall of the tube 13. The notch 29 forms a long opening in the axis direction 101 in the peripheral wall of the tube 13. The parts of the periphery of the notch 29 constitute the tip 31 of the first tube 21 and a base end 32 of the second tube 22, respectively. More specifically, the first tube 21 constitutes the first lumen 24 as an integral lumen while defining the base end 26 and the tip 31, which is a part of the periphery of the notch 29, as both ends. The second tube 22 constitutes the second lumen 28 as an integral lumen while defining the base end 32 and a tip 33, which is a part of the periphery of the notch 29, as both ends. Thus, a guidewire can be inserted to/pulled out from the first lumen 24 or the second lumen 28 through the notch 29. More specifically, the opening formed by the notch 29 has a sufficient dimension such that two or more guidewires can be inserted to/pulled out from the first lumen 24 or the second lumen 28. A part of the remaining portion of the peripheral wall that is opened by the notch 29 serves as the connection portion 23. More specifically, the connection portion 23 is constituted by a part of the peripheral wall of the tube 13.

The connection portion 23 extends in the axis direction 101 and both the ends are continuous to the first tubular body 21 and the second tubular body 22, respectively. In other words, the first tubular body 21 and the second tubular body 22 are connected to each other by the connection portion 23 at an interval equivalent to the dimension of the notch 29 in the axis direction 101. As described above, since the first tubular body 21 and the second tubular body 22 are constituted by the single tube 13, each axis of the first tubular body 21 and the second tubular body 22 connected by the connection portion 23 is the same. Thus, two or more guidewires extending along the axis direction 101 can be continuously inserted to the first lumen of 24 and the second lumen 28.

Although not shown in detail in each drawing, the sub-lumen 25 described above extends along the inner surface of the connection portion 23 and the core material 27 provided in the sub-lumen 25 is disposed in the connection portion 23 in the axis direction 101. When the connection portion 23 is supported by the core material 27 in the axis direction 101, the connection portion 23 has rigidity that allows elastic deformation in the axis direction 101 in accordance with the curved shape of the arterial blood vessel or the like and that prevents buckling in the axis direction 101.

As shown in FIGS. 5 and 7, a slit 34 is formed in the second tube 22 along the axis direction 101. The slit 34 is substantially linearly formed from the base end 32 to the tip 33 of the second tube 22 and cuts the peripheral wall of the second tube 22 in the thickness direction (the diameter direction). The slit 34 is closed unless external force acts on the second tube 22. When external force acts thereon in such a manner as to enlarge the diameter of the second tube 22, the second tube 22 is elastically deformed and opened.

Hereinafter, a method for using the twist releasing apparatus 10 will be described.

When two or more guidewires are passed through the guiding catheter and then twisted, the twist releasing apparatus 10 releases the twist of the two or more guidewires when inserted to/pulled out from the guiding catheter. The two or more guidewires are not particularly limited insofar as the number of the guidewires is two or more. In this embodiment, a method for using the twist releasing apparatus 10 will be described based on the assumption the two guidewires 51 and 52 are passed through the guiding catheter.

When the twist releasing apparatus 10 is used, the guiding catheter is inserted to the arterial blood vessel or the like, and the two guidewires 51 and 52 are passed through the guiding catheter so that the tip of each of the guidewires 51 and 52 reach the narrowed portion of the coronary arteries or the like. Such insertion of the guiding catheter and passing of the guidewires 51 and 52 are performed by publicly techniques described in Japanese Unexamined Patent Application Publication No. 2006-326226 or 2006-230442, for example. Thus, the detailed description thereof is omitted here.

When the guidewires 51 and 52 are twisted in the guiding catheter inserted to the arterial blood vessel or the like as described above, the twist releasing apparatus 10 is used. In other words, unless the guidewires 51 and 52 are twisted in the guiding catheter, a balloon catheter or the like may be inserted while being guided by the guidewires 51 and 52 without using the twist releasing apparatus 10.

Figure 8:
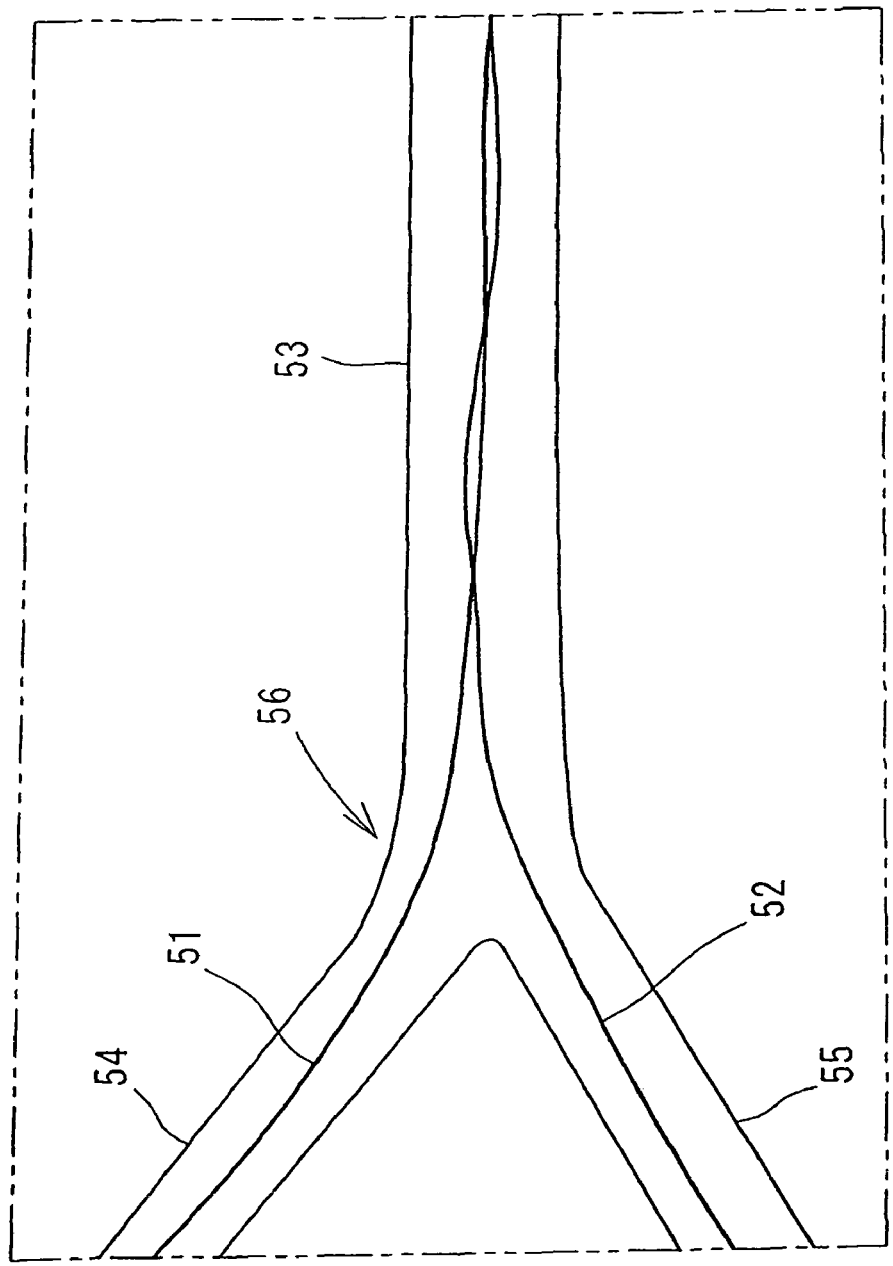
FIG. 8 is a schematic view for describing a method for releasing twist of guidewires 51 and 52 by the twist releasing apparatus 10.

As shown in FIG. 8, it is assumed that the two guidewires 51 and 52 are inserted to a second blood vessel 54 and a third blood vessel 55, respectively, which are branched in a Y shape from a first blood vessel 53 then twisted in the first blood vessel 53. The guidewires 51 and 52 may be twisted either inside or outside the guiding catheter. The guiding catheter is omitted in each drawing.

As shown in FIG. 8, when the guidewires 51 and 52 are twisted, the base ends of the guidewires 51 and 52 projected to the hand side of the guiding catheter are first inserted to the second lumen 28 and then the first lumen 24. In detail, the base ends of the guidewires 51 and 52 are inserted to the second lumen 28 from the tip 33 of the second tubular body 22 to be projected from the base end 32 of the second tubular body 22, and then are inserted to the first lumen 24 from the tip 31 of the first tubular body 21 to be project from the base end 26 of the first tubular body 21. Thus, the guidewires 51 and 52 are continuously passed through the second lumen 28 and the first lumen 24.

Subsequently, the tube 13 of the twist releasing apparatus 10 is inserted to the guiding catheter with the second tubular body 22 positioned at the head. As described above, since the tube 13 has an outer diameter that allows to pass through the guiding catheter, the second tubular body 22, the connection portion 23, and the first tubular body 21 integrally constituted by the tube 13 are successively inserted to the guiding catheter. Furthermore, by moving the tube 13 in the guiding catheter to the tip side, the shaft 12 is also inserted to the guiding catheter. By operating the handle portion 11 or the shaft 12 of the twist releasing apparatus 10, the tube 13 is moved to the tip of the guiding catheter, and then the second tube 22 is projected from the tip of the guiding catheter. The position of the second tube 22 is grasped by detecting the X-ray marker 30 by X-ray imaging.

Figure 9:
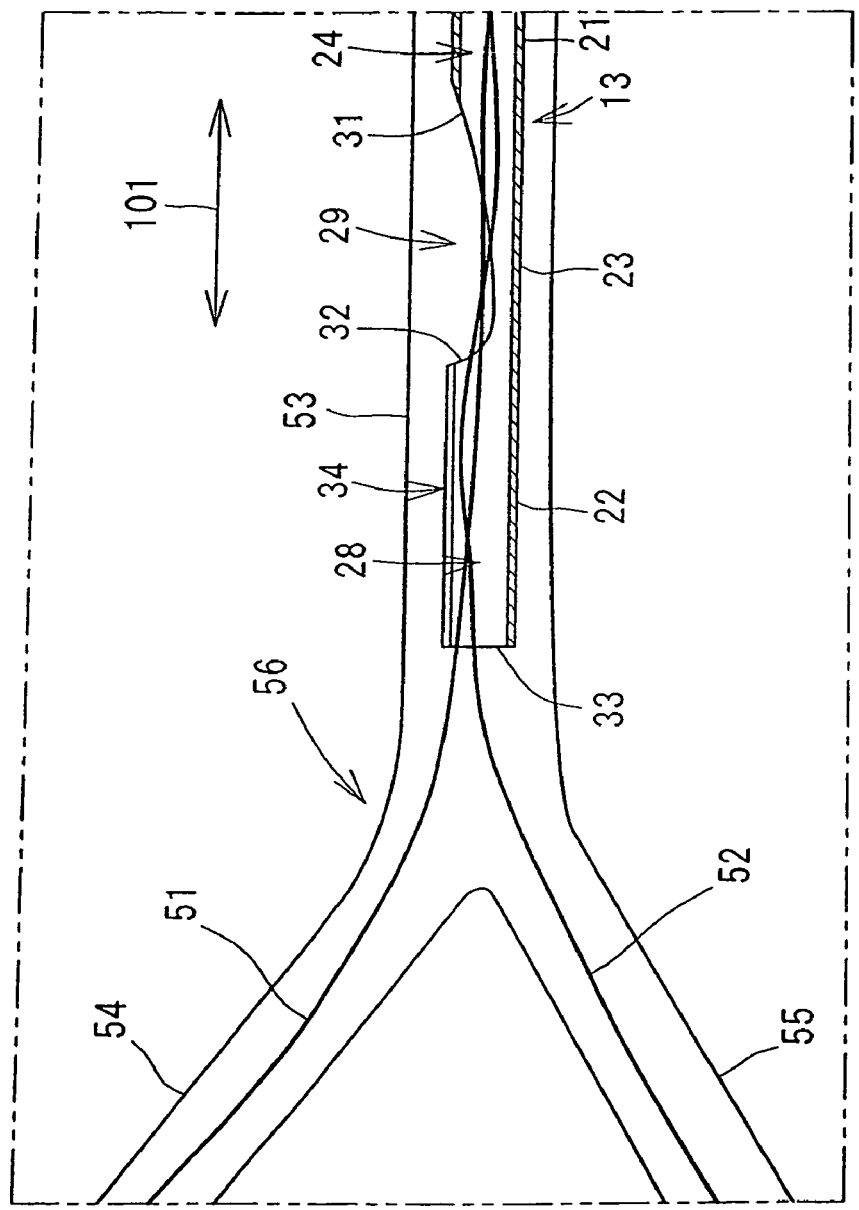
FIG. 9 is a schematic view for describing a method for releasing the twist of the guidewires 51 and 52 by the twist releasing apparatus 10.

The tube 13 projected from the tip of the guiding catheter is guided by the guidewires 51 and 52 to be moved through the first blood vessel 53 to the second blood vessel 54 and the third blood vessel 55 with the second tube 22 positioned at the head as shown in FIG. 9. In this case, the guidewires 51 and 52 are passed through the first lumen 24 and the second lumen 28 while the guidewires 51 and 52 being twisted.

When the tip 33 of the second tube 22 reaches a branch position 56 between the second blood vessel 54 and the third blood vessel 55, the second tube 22 is guided by either one of the guidewires 51 and 52 divided along the second blood vessel 54 and the third blood vessel 55 at the branch position 56 to move to either one of the second blood vessel 54 or the third blood vessel 55. Here, it is assumed that the second tube 22 is guided by the guidewire 52 to the third blood vessel 55.

Figure 10:
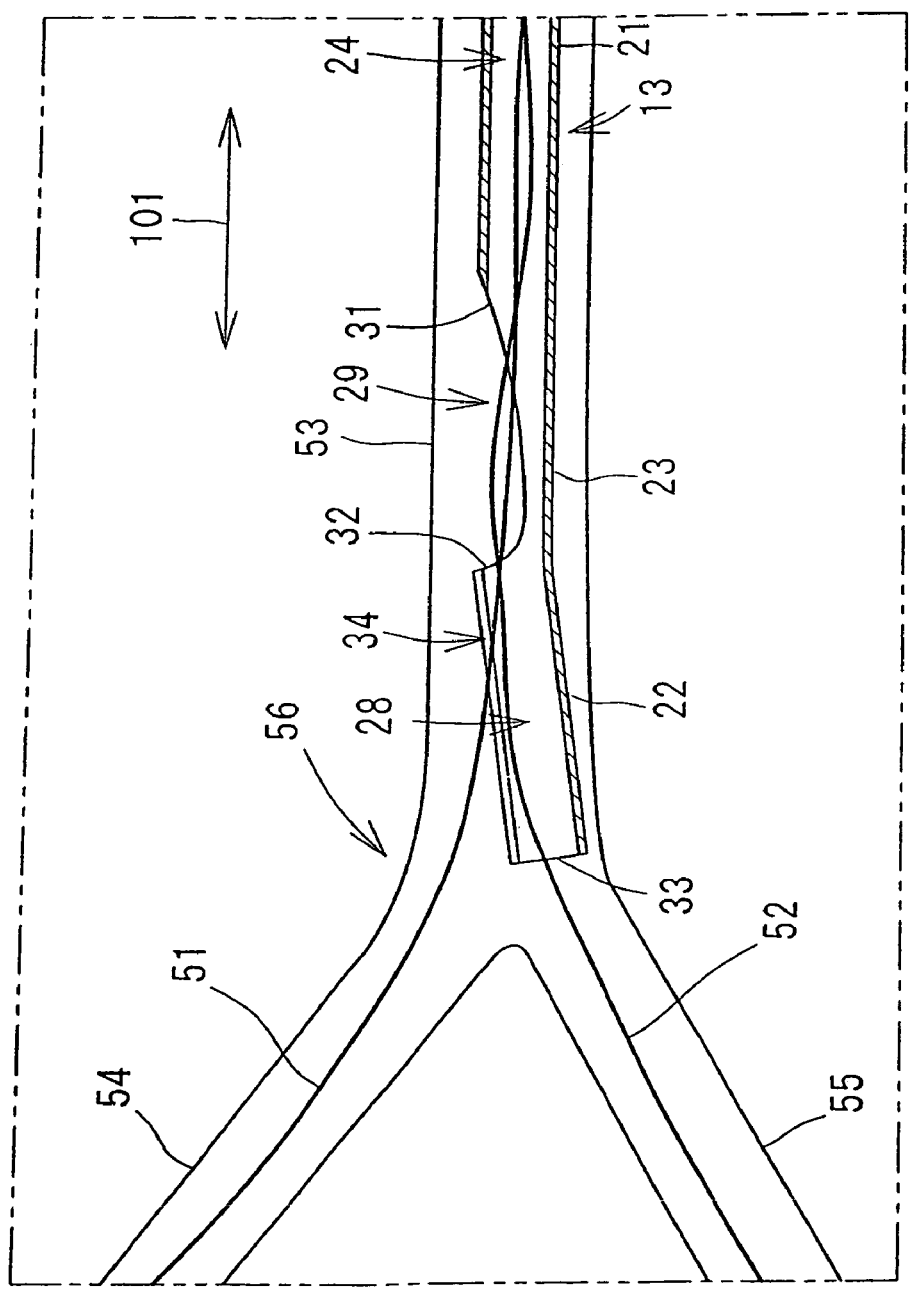
FIG. 10 is a schematic view for describing a method for releasing the twist of the guidewires 51 and 52 by the twist releasing apparatus 10.

When the second tube 22 is guided by the guidewire 52 to move to the third blood vessel 55 as shown in FIG. 10, the force enlarging the diameter of the second lumen 28 acts on the second tube 22 from the guidewires 51 and 52 due to the fact that the guidewires 51 and 52 are divided. By the force, the second tube 22 is elastically deformed to open the slit 34.

Therefore, as shown in FIG. 10, the second tube 22 is guided by the guidewire 52 to move to the third blood vessel 55 and simultaneously the guidewire 51 moves toward the base end 32 from the tip 33 of the second tube 22 while passing through the opened slit 34. Then, when the guidewire 51 comes out from the slit 34 thorough the base end 32 of the second tubular body 21, the guidewire 51 comes out from the second lumen 28 as shown in FIG. 11.

Figure 11:
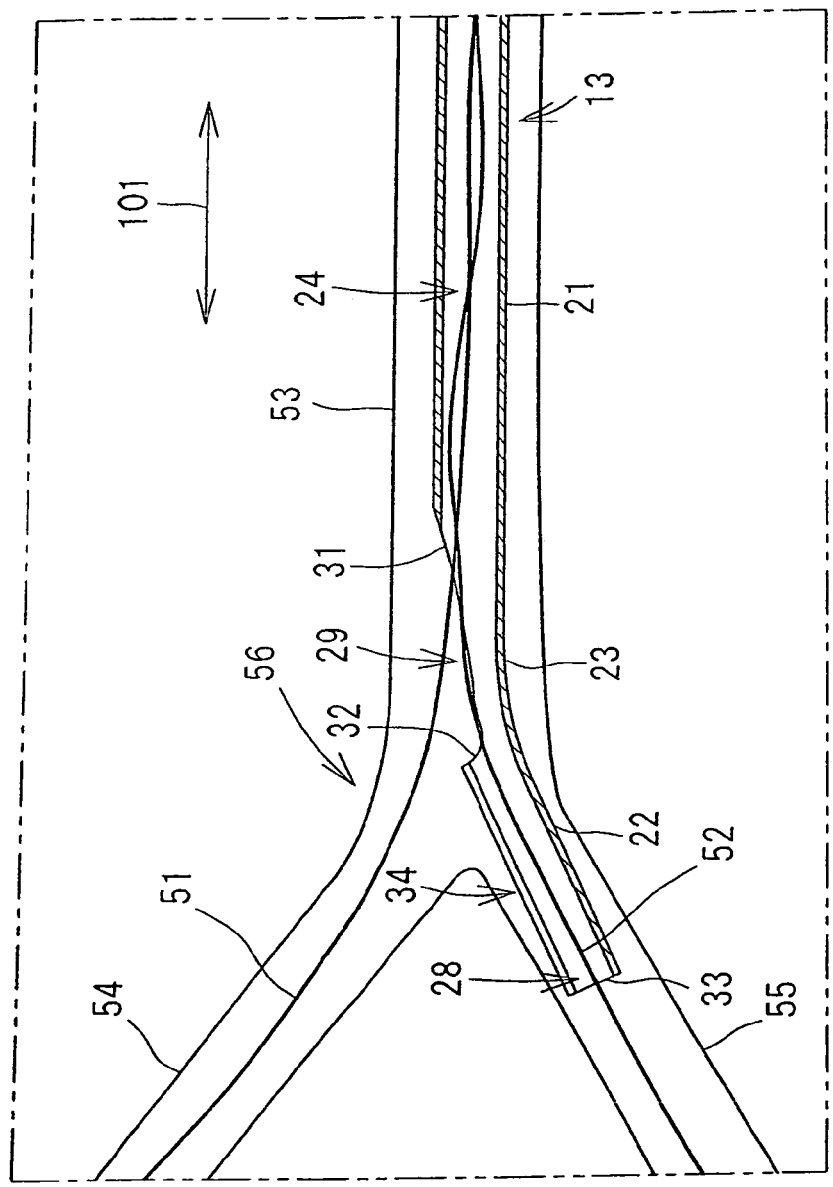
FIG. 11 is a schematic view for describing a method for releasing the twist of the guidewires 51 and 52 by the twist releasing apparatus 10.

As shown in FIG. 11, when the guidewire 51 comes out from the second lumen 28, only the guidewire 52 is passed through the first lumen 24 and the second lumen 28 and the guidewire 51 is passed through only the first lumen 24 and is projected from the notch 29 to the outside of the tube 13. Moreover, only the second tube 22 moves toward the third blood vessel 55 and the first tube 21 remains at the first blood vessel 53 before the branch position 56. In this case, the connection portion 23 is in a shape of curving the second tube 22 in the axis direction 101 relative to the first tube 21, so that only the second tube 22 is made to enter the third blood vessel 55.

Figure 12:
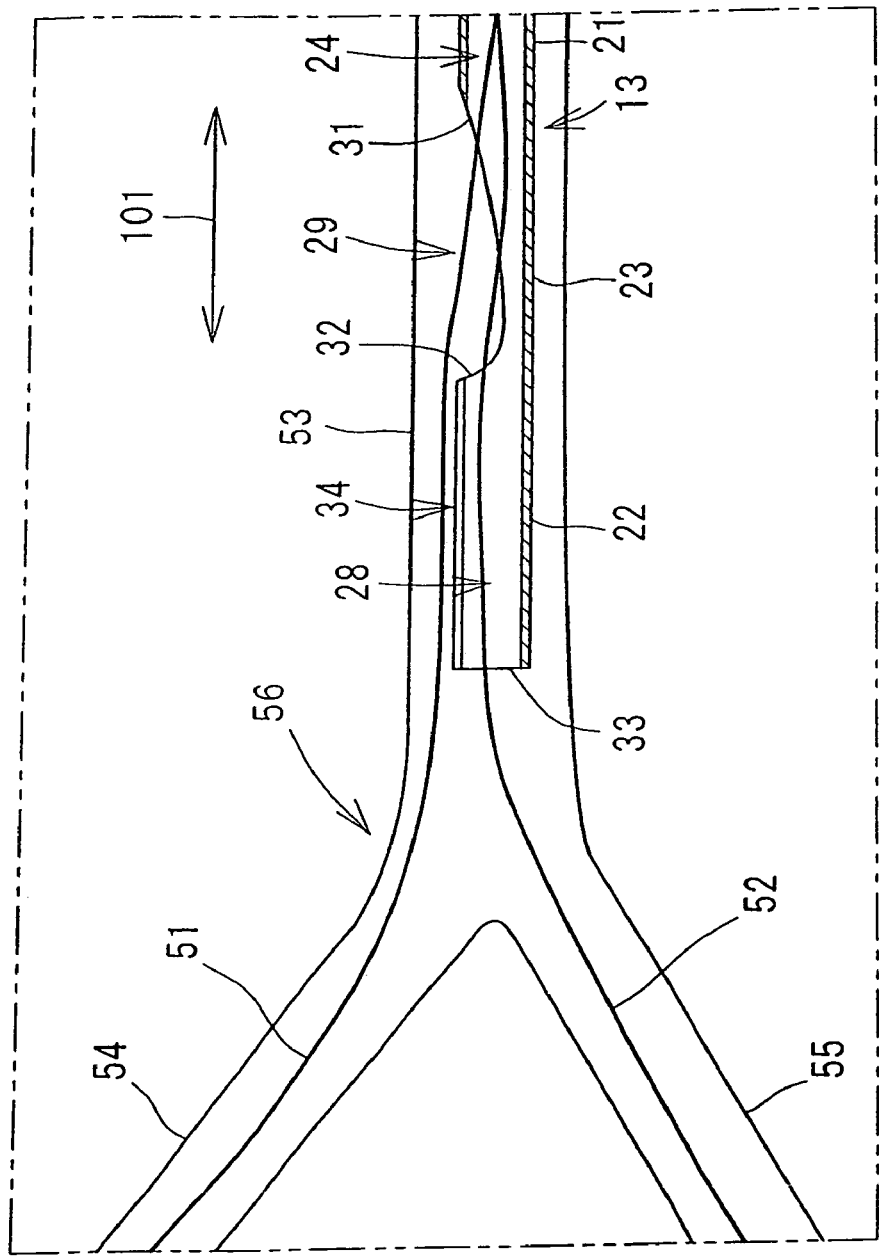
FIG. 12 is a schematic view for describing a method for releasing the twist of the guidewires 51 and 52 by the twist releasing apparatus 10.

Subsequently, the handle portion 11 or the shaft 12 is operated, and the tube 13 is pulled out from the guiding catheter. Then, as shown in FIG. 12, the tube 13 returns to the guiding catheter side (right side in FIG. 12) through the first blood vessel 53 in a state where only the guidewire 52 is passed through the first lumen 24 and the second lumen 28 and the guidewire 51 is passed through only the first lumen 24 and is projected from the notch 29 to the outside of the tube 13. When the tube 13 returns to the guiding catheter side through the first blood vessel 53, the tube 13 is settled in the guiding catheter, but the guiding catheter is omitted in each drawing.

As described above, only the guidewire 52 among the two guidewires 51 and 52 passed through the guiding catheter is continuously passed through the second lumen from the first lumen 24 when the tube 13 is pulled out from the guiding catheter. In contrast, the guidewire 51 passes through the notch 29, without passing the second lumen 28, from the first lumen 24. More specifically, the guidewires 51 and 52 pass through different paths at the notch 29 after passing through the first lumen 24. Thus, when the tube 13 is pulled out from the guiding catheter, the twist of the guidewires 51 and 52 and other guidewires is released. Then, finally, the tube 13 is completely pulled out from the guiding catheter.

As described above, according to the twist releasing apparatus 10, the guidewires 51 and 52 twisted in the guiding catheter are passed through the first lumen 24 and the second lumen 28, the tube 13 is inserted to the guiding catheter to be projected from the tip of the guiding catheter with the second tube 22 positioned at the head, only the second tube 22 is guided by either one of the two guidewires 51 and 52, e.g., the guidewire 52, to be directed to the third blood vessel 55, the guidewire 51 is passed through the slit 34 of the second tube 22 to be pulled out from the second lumen 28, only the guidewire 52 is passed through the first lumen 24 and the second lumen 28, and the guidewire 51 can be passed through only the first lumen 24 and projected from the notch 29 to the outside of the tube 13. Then, in the state, when the tube 13 is pulled out from the guiding catheter, the respective guidewires 51 and 52 are passed through different paths in the guiding catheter, whereby the twist of the guidewires 51 and 52 is released. Therefore, the twist of the guidewires 51 and 52 passed through the guiding catheter can be easily released without pulling out the guidewires 51 and 52 from the guiding catheter.

Moreover, since the first tube 21, the second tube 22, and the connection portion 23 can be formed from the single tube 13, the production of the twist releasing apparatus 10 is facilitated. Since projection portions, such as projections or level differences, can be reduced as much as possible in the outer shape of the first tube 21, the second tube 22, and the connection portion, the first tube 21, the second tube 22, and the connection portion that hardly damage blood vessels can be achieved.

Since the first tube 21 is supported by the core material 27 along the axis direction 101, the first tube 21 becomes difficult to buckle during the operation. Since the core material 27 is formed in the sub-lumen 25 which is another space different from the first lumen 24, the core material 27 is not twisted with the guidewires 51 and 52.

Since the X-ray marker is provided in the second tube 22, the operation can be performed while confirming the position of the second tube 22 in blood vessels by X-ray imaging.

The description of this embodiment is directed to the case where the two guidewires 51 and 52 are passed through the guiding catheter and twisted. However, the twist releasing apparatus 10 can be used also in a case where three or more guidewires are passed through the guiding catheter and twisted. When the number of the guidewires is three or more, the twist of the two remaining guidewires equivalent to the guidewire 51 described above is released as follows. In the same manner as in the operation for releasing the twist of the single guidewire, by passing only one guidewire of the remaining two guidewires through the second lumen 28, the twist of the other two guidewires is released.

In this embodiment, although the first tube 21, the second tube 22, and the connection portion 23 are constituted from the single tube 13, it is a matter of course that the first tubular body, the second tubular body, and the connection member according to the invention may be individually constituted as separate members. Therefore, for example, the guidewire twist releasing device according to the invention may be achieved by a structure in which a tube as the first tubular body and a tube as the second tubular body are formed as separate members and the two tubes are connected by a bar-shaped material as a connection member.

Although the X-ray marker 30 is embedded in the second tube 22 in this embodiment, an X-ray marker 31 may be embedded in the first tube 21.

Figure 13:
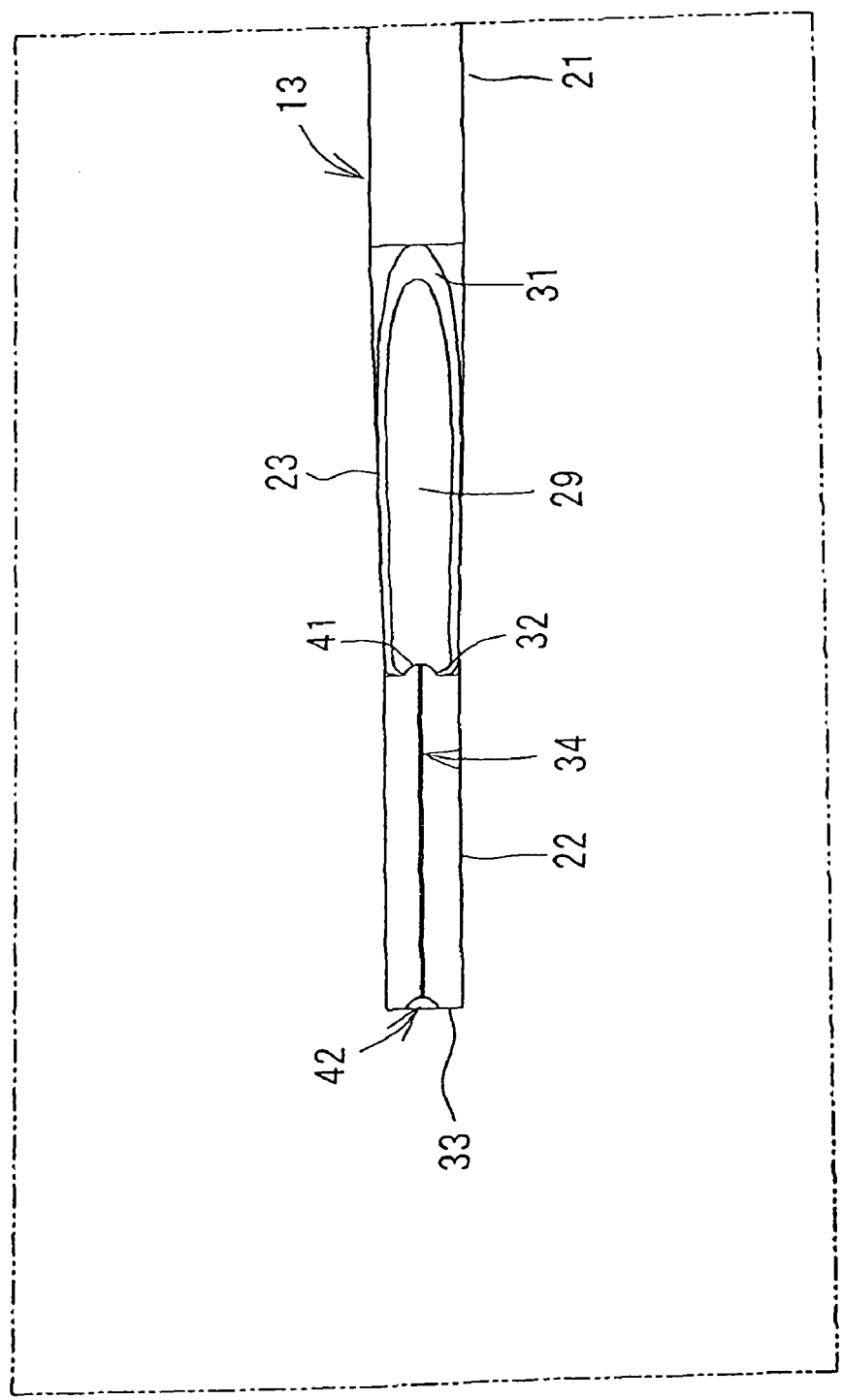
FIG. 13 is an enlarged view showing a modification of the embodiments.

Hereinafter, a modification of the embodiment described above will be described. In this modification, the structure is the same as that of the embodiment described above, except that the shape of the base end 32 and the tip 33 of the second tube 22 are different. Therefore, only the base end 32 and the tip 33 of the second tube 22 that are different in the shape will be described in detail, and the description for other members is omitted. In FIG. 13, members designated by the same reference numbers as those of the embodiment described above are the same members as those designated by the same reference numbers in the embodiment described above.

As shown in FIG. 13, one portion of the base end 32 of the second tube 22 where the slit 34 is formed serves as a protrusion 41 extending to the first tube 21 side along the axis direction 101. The base end 32 on which the protrusion 41 is provided is equivalent to the first end of the second tubular body in the invention.

Moreover, as shown in FIG. 13, one portion of the tip 33 of the second tube 22 in which the slit 34 is formed serves as a recess 42 that is recessed along the axis direction 101. The tip 33 in which the recess 42 is formed is equivalent to the second end of the second tubular body in the invention.

In the same manner as in the embodiment described above, when the twist of the two guidewires 51 and 52 is released, the guidewire 51 moves to the base end 32 from the tip 33 of the second tube 22 while passing through the opened slit 34, and then comes out from the second lumen 28 (FIG. 10). When the guidewire 51 enters the slit 34 from the tip 33 of the second tube 22, the guidewire 51 is guided to the slit 34 while defining the recess 42 as a guiding portion, which facilitates the entry of the guidewire 51 into the slit 34.

In the same manner as in the embodiment described above, when the twist of the two guidewires 51 and 52 is released, the guidewire 51 is passed through only the first lumen 24 to be projected from the notch 29 to the outside of the tube 13 (FIG. 12). When the tube 13 is pulled out from the guiding catheter, the guidewire 51 contacts the base end 32 of the second tube 22.

The direction in which the protrusion 41 extends is a direction in which the tube 13 is pulled out. In order for the guidewire 51 to enter the slit 34 passing over the protrusion 41, the guidewire 51 needs to move in the direction in which the tube 13 be pulled out. However, when the tube 13 is pulled out, the guidewire 51 is relatively moved to the base end 32 side of the second tube 22 in the notch 29. Therefore, the guidewire 51 hardly moves against the movement in the direction in which the tube 13 is pulled. Therefore, the protrusion 41 prevents the guidewire 51 from accidentally entering the slit 34 to re-enter the second lumen 28.

DESCRIPTION OF REFERENCE NUMERALS

10. Twist releasing apparatus (Guidewire twist releasing device)
12. Shaft (Long member)
13. Tube (Tubular body)
21. First tube (First tubular body)
22. Second tube (Second tubular body)
23. Connection portion (Connection member)
24. First lumen
25. Sub-lumen
27. Core material
28. Second lumen
30. X-ray marker (Marker)
32. Base end (First end)
33. Tip (Second end)
34. Slit
41. Protrusion
42. Recess
51, 52. Guidewire

The invention claimed is:

1. A guidewires twist releasing device, which releases twist of two or more guidewires passed through a guiding catheter, the device comprising:

a long member that can be inserted into and pulled out from the guiding catheter;

a first tubular body provided at the tip of the long member in such a manner as to be inserted into and pulled out from the guiding catheter and has a first lumen through which the two or more guidewires can be passed;

a second tubular body that is disposed through a gap at a tip side relative to the first tubular body in an axial direction of the first tubular body in such a manner as to be inserted into and pulled out from the guiding catheter and has a second lumen through which the two or more guidewires can be passed;

a connection member for connecting the first tubular body and the second tubular body and including the gap so as to define a notch between the first tubular body and the second tubular body, each of the first tubular body, the second tubular body and the connection member being formed into an integral tubular body so as to form a continuous guidewire insertion body through which the two or more guidewires can be continuously passed from the first lumen to the second lumen, the notch defined between the first tubular body and the second tubular body defining an opening in the tubular body, the second tubular body having a slit formed in an axial direction and can be elastically deformed so that the slit opens upon exertion of a predetermined force exerted on the second tubular body; and the connection member being able to be elastically deformed into a curved shape in an axial direction of the first tubular body, the slit opening of the second tubular body forming an exit for one of the two more guidewires from the second tubular body along a first guidewire pathway, the first guidewire pathway extending from the first lumen of the first tubular body to the slit opening and through the notch so that the one of the two or more guidewires is passed only along the first guidewire pathway through the first lumen of the first tubular body, and the one of the two or more guidewires is caused to travel from the first lumen of the first tubular body and along said first guidewire pathway to an intended blood vessel whereupon twisting of the two or more guidewires is released so that the one of the two or more guidewires is separated and untwisted from at least one or more of the two or more guidewires, respectively, upon pulling of the long member out of the catheter, the other of the two or more guidewires being passed through both the first lumen of the first tubular body and the second lumen of the second tubular body so as to travel along a second guidewire pathway diverging from the first pathway and extending from the first lumen of the first tubular body to the second lumen of the second tubular body and toward an intended blood vessel upon pulling of the long member out of the catheter.

2. The guidewires twist releasing device according to claim 1, wherein, at a first end facing the first tubular body among both the ends in an axial direction of the second tubular body, a protrusion in which one portion where the slit is formed extends in the axial direction is provided.

3. The guidewires twist releasing device according to claim 2, wherein, at a second end not facing the first tubular body among both the ends in an axial direction of the second tubular body, a recess in which one portion where the slit is formed is recessed in the axial direction is provided.

4. The guidewires twist releasing device according to claim 3, wherein a marker detectable by radiation is provided in the first tubular body.

5. The guide wires twist releasing device according to claim 2, wherein the first tubular body has a sub-lumen serving as another space different from the first lumen, and a core material is provided in the sub-lumen.

6. The guidewires twist releasing device according to claim 5, wherein a marker detectable by radiation is provided in the first tubular body.

7. The guidewires twist releasing device according to claim 2, wherein a marker detectable by radiation is provided in the first tubular body or the second tubular body.

8. The guidewires twist releasing device according to claim 1, wherein, at a second end not facing the first tubular body among both the ends in an axial direction of the second tubular body, a recess in which one portion where the slit is formed is recessed in the axis direction is provided.

9. The guide wires twist releasing device according to claim 8, wherein the first tubular body has a sub-lumen serving as another space different from the first lumen, and a core material is provided in the sub-lumen.

10. The guidewires twist releasing device according to claim 9, wherein a marker detectable by radiation is provided in the first tubular body.

11. The guidewires twist releasing device according to claim 8, wherein a marker detectable by radiation is provided in the first tubular body or the second tubular body.

12. The guidewires twist releasing device according to claim 1, wherein the first tubular body has a sub-lumen serving as another space different from the first lumen, and a core material is provided in the sub-lumen.

13. The guidewires twist releasing device according to claim 12, wherein a marker detectable by radiation is provided in the first tubular body.

14. The guidewires twist releasing device according to claim 1, wherein a marker detectable by radiation is provided in the first tubular body.

* * * * *